United States Patent [19]
Merianos

[11] 4,087,451
[45] May 2, 1978

[54] 2,3-DIHALO-1,4-DITHIOCYANO-2-BUTENES AND THEIR HOMOLOGS

[75] Inventor: John J. Merianos, Jersey City, N.J.
[73] Assignee: Kewanee Industries, Inc., Bryn Mawr, Pa.
[21] Appl. No.: 789,215
[22] Filed: Apr. 20, 1977
[51] Int. Cl.² .................... C07C 161/02; A01N 9/18
[52] U.S. Cl. .................................. 260/454; 424/302
[58] Field of Search ........................................ 260/454

[56] References Cited

U.S. PATENT DOCUMENTS 3,212,963  10/1965  Wehner ................................ 260/454

Primary Examiner—Joseph Paul Brust
Assistant Examiner—Robert C. Whittenbaugh
Attorney, Agent, or Firm—Arthur A. Jacobs

[57] ABSTRACT

Antimicrobial compounds having the structure:

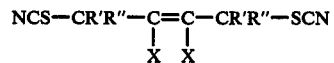

wherein X is chlorine, bromine or iodine and R' and R" may be the same or different and are selected from the group consisting of hydrogen and acyclic hydrocarbon monovalent radicals having 1 to 8 carbon atoms.

7 Claims, No Drawings

2,3-DIHALO-1,4-DITHIOCYANO-2-BUTENES AND THEIR HOMOLOGS

This invention relates to a new class of compounds which have antimicrobial properties and also fire retardant properties; More specifically this invention relates to 2, 3-dihalo-1,4-dithiocyano-2-butene and certain homologs of this compound.

The compounds of the present invention may be represented by the structural formula

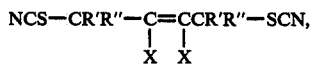

wherein X represents either chlorine, bromine or iodine, and R' and R" may be the same of different and are selected from the group consisting of hydrogen and acyclic hydrocarbon monovalent radicals having from 1 to 8 carbon atoms. Preferred compounds are those where (a) R'=R"=H, (b) R'=H, R"=CH$_3$, (c) R'=CH$_3$, R"=CH$_3$, (d) R'=CH$_3$, R"=C$_2$H$_5$, and (e) R'=CH$_3$, R"=CH$_2$CH (CH$_3$)$_2$.

Ordinarily, dithiocyano compounds are synthesized by the addition of thiocyanogen to alkenes, but this leads to saturated vicinal dithiocyano products and not to the unsaturated 1,4-dithiocyano compounds of the present invention.

In accordance with the present invention, halogenated dihalo-bis-thiocyano compounds were synthesized circuitously from the corresponding 2,3-dihalo-2-butene-1,4-diols and their homologs by a two step synthesis. In the first step, two chlorine atoms were substituted for the two hydroxyl groups using thionyl chloride as the reagent. In the second step, two thiocyano groups displaced the two chlorine atoms in a straightforward substitution reaction using thiocyanate ions, and aqueous methanol as a solvent, at reflux temperatures.

The complete synthesis may be represented by the equations

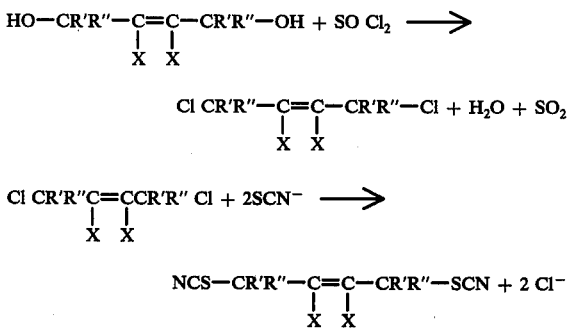

The following examples disclose experimental details of the synthesis of the compounds of the present invention; however, they are meant to be illustrative of the procedure and not necessarily limitative.

The 2,3-dihalo-2-butene-1,4-diols were prepared by a method which approximated the method of Kleinert and Fuerst, "J. Prakt. Chem." 36 (5–6) 252-5 (1967) Ger. (See Chem. Abstracts 68 68,394J). No effort was made to ascertain the optimum conditions for maximum yield.

EXAMPLE 1

0.5 mole of 2-butyne-1,4-diol (43 grams) was stirred with about 500 ml. of cold water and 10 grams of cupric chloride, surrounded by an ice bath, and chlorine gas was bubbled into the mixture until about 40 grams of chlorine had been absorbed, this taking place over a period of about 2 hours. Stirring was continued for about one more hour, then the mixture was filtered under suction and washed on the filter paper with two 500 ml. portions of cold 5% sodium bicarbonate solution and two 500 ml. portions of cold water. The dried crude residue, after recovery, weighed about 70 grams, which is about 90% of theory.

EXAMPLE 2

The procedure of Example 1 was repeated, except that 81 grams of liquid bromine were added dropwise instead of 40 grams of gaseous chlorine, and cupric bromide replaced cupric chloride. The dried crude residue, after recovery, weighed about 100 grams, which is about 90% of theory.

EXAMPLE 3

The procedure of Example 1 was repeated, except that a cold solution of 130 grams of iodine in 1 liter of 20% aqueous potassium iodide was added slowly, instead of gaseous chlorine, and cupric iodide replaced the cupric chloride. The dried crude residue, after recovery, weighed about 170 grams, which is almost 100% of theory.

The crude dihalobutenediols were used in the succeeding steps without recrystallization. The material could, however, if desired, be recrystallized out of mixtures of organic solvents such as methanol, ethylacetate and hexane in various proportions.

EXAMPLE 4

246 grams of 2,3-dibromo-2-butene-1,4-diol (1 mole) were added to 360 grams of thionyl chloride (3 moles) and 1 liter of benezene, with constant stirring. The mixture, while under agitation, was warmed to about 40°–50° C, but there was no evidence of reaction; however, upon the addition of a few drops of dimethyl formamide, a vigorous endothermic reaction ensued during which the temperature dropped to about 30° C and much gaseous hydrogen chloride and sulfur dioxide was liberated. Stirring was continued until no more gases appeared to be evolved (about 2 hours). The excess thionyl chloride and benzene were stripped from the mixture by distillation, leaving behind the solid residue which was 1,4-dichloro-2,3-dibromo-2-butene. The product was then washed with petroleum ether. The yield was 279 grams, which is virtually 100%. The melting point was between 58°–61° C. No further purification was required for the next step.

EXAMPLE 5

20.0 grams of potassium thiocyanate (0.2 mole) were dissolved in 50 ml. of water and 25 ml. of methanol. 28.3 grams of 1,4-dichloro-2,3-dibromo-2-butene were dissolved in 75 ml. of methanol. The solution of the organic compound was added slowly to the solution of the inorganic compound, with continued stirring, and the mixture was then heated to about 60° to 70° C for about 2 hours while being stirred. A white precipitate was deposited during the reaction. This precipitate was collected and washed by shaking three times with 100 ml. portions of water. Then it was filtered and dried at about 50°–60° C. The yield was 31.5 grams, and was found to melt at 175°–177° C. It was colored offwhite.

2-butene-1,4-diols, and many of their homologs, such as the 1,4-dimethyl homolog, the 1,1,4,4-tetramethyl homolog, the 1,4-dimethyl-1,4-diethyl homolog, the 1,4-dimethyl-1,4-diisobutyl homolog, and the like, all of which are utilizable in the present invention, are commercially available from Air Products and Chemicals, Inc. Allentown, Pa. and GAF, New York, NY.

The invention claimed is:

1. An antimicrobial compound having the structure:

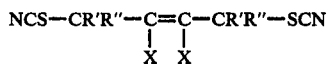

wherein X is the same and is selected from the group consisting of chlorine, bromine and iodine, and wherein R' and R" may be the same or different and are selected from the group consisting of hydrogen and acyclic monovalent branched and unbranched saturated hydrocarbon radicals having 1 to 8 carbon atoms.

2. The compound of claim 1 wherein R' is selected from the group consisting of H and $CH_3$ and R" is selected from the group consisting of H, $CH_3$, $C_2H_5$ and $CH_2CH(CH_3)_2$.

3. The compound of claim 1 wherein R' and R" are hydrogen.

4. The compound of claim 1 wherein R' is hydrogen and R" is $CH_3$.

5. The compound of claim 1 wherein R' is $CH_3$ and R" is $CH_3$.

6. The compound of claim 1 wherein R' is $CH_3$ and R" is $C_2H_5$.

7. The compound of claim 1 wherein R' is $CH_3$ and R" is $CH_2CH(CH_3)_2$.

* * * * *